US012778877B2

(12) United States Patent
Skubsch et al.

(10) Patent No.: US 12,778,877 B2
(45) Date of Patent: Nov. 3, 2026

(54) PARTICULARLY NATURAL OIL SUBSTITUTE FOR COSMETIC PREPARATIONS

(71) Applicant: BEIERSDORF AG, Hamburg (DE)

(72) Inventors: Kerstin Skubsch, Prisdorf (DE); Kerstin Franck, Quickborn (DE); Nadine Voigt, Hamburg (DE); Jette Mareike Neben, Hamburg (DE); Svea Wischhoefer, Hamburg (DE); Katharina Herwig, Hamburg (DE); Katrin Rupp, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 1216 days.

(21) Appl. No.: 17/753,225

(22) PCT Filed: Aug. 21, 2020

(86) PCT No.: PCT/EP2020/073491

§ 371 (c)(1),
(2) Date: Feb. 24, 2022

(87) PCT Pub. No.: WO2021/037716

PCT Pub. Date: Mar. 4, 2021

(65) Prior Publication Data

US 2022/0296494 A1 Sep. 22, 2022

(30) Foreign Application Priority Data

Aug. 27, 2019 (DE) ......................... 102019212794.0

(51) Int. Cl.
*A61K 8/92* (2006.01)
*A61K 8/06* (2006.01)
*A61K 8/73* (2006.01)

(52) U.S. Cl.
CPC .............. *A61K 8/922* (2013.01); *A61K 8/062* (2013.01); *A61K 8/732* (2013.01); *A61K 2800/34* (2013.01)

(58) Field of Classification Search
None
See application file for complete search history.

(56) References Cited

U.S. PATENT DOCUMENTS

| | | | |
|---|---|---|---|
| 6,248,338 B1 | 6/2001 | Mueller et al. | |
| 2009/0192233 A1 | 7/2009 | Brinkmann | |
| 2015/0328099 A1* | 11/2015 | Angelino Dos Santos Teodoro | A61K 8/34 424/68 |
| 2020/0022899 A1* | 1/2020 | Roux | A61K 8/922 |
| 2021/0338542 A1 | 11/2021 | Raschke et al. | |
| 2022/0323332 A1 | 10/2022 | Skubsch et al. | |

FOREIGN PATENT DOCUMENTS

| | | | |
|---|---|---|---|
| BR | PI0504733 | A | 9/2007 |
| DE | 19627498 | A1 | 1/1998 |
| DE | 1022017 | A2 | 7/2000 |
| DE | 10216508 | A1 | 10/2003 |
| DE | 10216511 | A1 | 10/2003 |
| EP | 2011483 | A2 | 1/2009 |
| WO | 0200733 | A1 | 1/2002 |
| WO | 2007017196 | A2 | 2/2007 |
| WO | 2021037455 | A1 | 3/2021 |
| WO | 2021037714 | A1 | 3/2021 |
| WO | 2020043363 | A1 | 11/2021 |

OTHER PUBLICATIONS

Stephanie, PhD., Retrieved from <https://us.typology.com/library/what-is-olus-oil-and-what-is-its-utility>, Nov. 16, 2021 (Year: 2021).*
Olus Oil, Retrieved from <www.specialchem.com/cosmetics/inci-ingredients/olus-oil>, Nov. 14, 2022. (Year: 2022).*
Anonymous. "After Sun Repair Lotion" Sep. 21, 2011 (Sep. 21, 2011). retrieved from www.gnpd.com. abstract No. Database accession No. 1625513.
Anonymous. "Micellar Shampoo" Jun. 25, 2019 (Jun. 25, 2019). retrieved from www.gnpd.com. abstract No. Database accession No. 6658567.
Anonymous. "Illuminate Sheer Light Illuminator" Apr. 12, 2019 (Apr. 12, 2019). retrieved from www.gnpd.com. abstract No. Database accession No. 6479809.

* cited by examiner

*Primary Examiner* — Nannette Holloman
(74) *Attorney, Agent, or Firm* — Abel Schillinger, LLP

(57) ABSTRACT

Use of a mixture of a) hydroxypropyl starch phosphate (INCI: Hydroxypropyl Starch Phosphate) and b) vegetable oils as a substitute for mineral oils and silicone oils in cosmetic preparations and use thereof in cosmetic preparations.

20 Claims, No Drawings

PARTICULARLY NATURAL OIL SUBSTITUTE FOR COSMETIC PREPARATIONS

BACKGROUND OF THE INVENTION

1. Field of the Invention

The present invention relates to a mixture of a) hydroxypropyl starch phosphate (INCI: Hydroxypropyl Starch Phosphate) and b) vegetable oils as a substitute for mineral and silicone oils in cosmetic preparations and to the use thereof in cosmetic preparations.

2. Discussion of Background Information

The desire to look beautiful and attractive is by nature ingrained in humans. Even though the ideal of beauty has undergone changes over time, people have always strived to have an immaculate appearance. An essential element of a beautiful and attractive appearance is the condition and appearance of the skin.

In order for the skin to perform its biological functions in full, it needs regular cleansing and care. Skin-care products, usually creams, ointments or lotions, are mostly used to moisturize the skin and replenish its natural oils. Often added to them are active substances that regenerate the skin and are intended, for example, to prevent and reduce its premature aging (e.g. formation of lines and wrinkles).

In addition to the cleansing and care of the skin, cosmetics have an aesthetic role too. They are intended to "improve" the external appearance of the user in accordance with the prevailing cultural perceptions. Cosmetics thus perform a psychological-social function, since they increase the (visual) attractiveness of users. First and foremost among them are "decorative" cosmetics that change the appearance of the user with the aid of coloring agents applied to the skin. However, cleansing and care products have an indirectly beneficial effect too, since a clean, healthy skin is the beauty ideal in humans.

Recent times have seen an increasing trend towards "natural" cosmetics, whose ingredients should ideally no longer derive from crude oil products or be chemically synthesized. This trend nowadays overlaps with the trend towards "vegan" products. The search for alternative ingredients meeting these criteria poses particular challenges to product developers. This is because substitution of known ingredients such as mineral oils, silicone oils and polyacrylates is practically always associated with disadvantages in terms of the use of the products. The products become unattractive from a sensory point of view which becomes unpleasantly apparent for example during spreading of the preparation on the skin and through inadequate absorbability. For instance the substitution of mineral oils, silicone oils and polyacrylates such as Carbomers, Acrylates/C10-30 Alkyl Acrylate Crosspolymer results in increased "whitening" when spreading the preparation onto the skin. This "whitening" occurs especially in preparations where the often employed xanthan gum (INCI: Xanthan Gum) is used instead of polyacrylates. Furthermore, the use of xanthan gum causes a stringy texture to occur, i.e. the formula forms strings when pulled apart between the fingers.

It is accordingly an object of the present invention to find a substitute for mineral oils and silicone oils in cosmetic preparations which has the same sensory properties (especially in terms of whitening, spreadability on the skin and absorbability) as the mineral and silicone oils.

It is a further object of the present invention to develop a cosmetic preparation (in particular an emulsion, here an O/W emulsion) which is free from mineral oils, silicone oils and polyacrylates which has the same sensory properties as conventional cosmetics containing these ingredients. These preparations should ideally be "vegan", i.e. do without ingredients of animal origin. It was further sought to develop a preparation whose ingredients are of a vegetable origin, wherein vegetable origin is to be understood as also including substances whose starting material is of vegetable origin and which are subsequently subjected to one or more derivatization steps (for example hydrolysis, esterification).

SUMMARY OF THE INVENTION

The objects were surprisingly achieved through the use of a mixture of a) hydroxypropyl starch phosphate (INCI: Hydroxypropyl Starch Phosphate) and b) vegetable oils as a substitute for mineral and silicone oils in cosmetic preparations.

The objects were surprisingly further achieved by a cosmetic preparation containing a mixture of a) hydroxypropyl starch phosphate (INCI: Hydroxypropyl Starch Phosphate) and b) vegetable oils, wherein the preparation is free from mineral oils, silicone oils, polyacrylates and xanthan gum.

It is advantageous according to the invention when the weight ratio of a) hydroxypropyl starch phosphate to b) the total amount of vegetable oils is from 2:1 to 1:20 and according to the invention preferably from 1:1 to 1:10.

In the context of the present disclosure, the term "according to the invention" always relates to preparations and uses according to the invention unless otherwise stated.

Hydroxypropyl starch phosphates as described in U.S. Pat. No. 6,248,338 are especially advantageous. The use of a hydroxypropyl di-starch phosphate, such as is commercially available from Nouryon as the product Structure® XL, is very particularly preferred.

It is advantageous according to the invention when the vegetable oils are selected from the group of the compounds *Persea gratissima* Oil, *Orbignya oleifera* Seed Oil, *Argania spinosa* Kernel Oil, *Prunus armeniaca* Kernel Oil, *Simmondsia chinensis* Seed Oil, *Cocos nucifera* Oil, *Silybum marianum* Seed Oil, *Oenothera biennis* Oil, *Olea europaea* Fruit Oil, *Helianthus annuus* Seed Oil, *Vitis vinifera* Seed Oil, *Cannabis sativa* Seed Oil, Olus Oil, Vegetable Oil, *Gossypium herbaceum* Seed Oil, *Arctium lappa* Seed Oil, *Macadamia ternifolia* Seed Oil, *Macadamia integrifolia* Seed Oil, *Zea mays* Germ Oil, *Prunus amygdalus dulcis* Oil, *Ricinus communis* Seed Oil, *Glycine soja* Oil, *Helianthus annuus* Hybrid Oil, *Sesamum indicum* Seed Oil, *Brassica campestris* Seed Oil.

Embodiments of the present invention that are advantageous according to the invention are further characterized in that the preparation contains one or more esters of caprylic acid and/or capric acid.

In such a case, it is preferable according to the invention when the esters of caprylic acid and/or capric acid are selected from the group of the compounds caprylic acid/capric acid triglycerides (INCI: Caprylic/Capric Triglyceride), caprylyl caprylate/caprate (INCI: Caprylyl Caprylate/Caprate), coco caprylate/caprate (INCI: Coco Caprylate/Caprate), coco glycerides (INCI: Coco Glycerides), ethylhexyl cocoate (INCI; Ethyl Hexyl Cocoate), decyl cocoate (INCI: Decyl Cocoate), isoamyl cocoate (INCI: Isoamyl Cocoate), dicaprylyl carbonate (INCI: Dicaprylyl Carbonate), coco caprylate (INCI: Coco-Caprylate).

It is advantageous according to the invention for the preparation according to the invention when the preparation contains the hydroxypropyl starch phosphate (INCI: Hydroxypropyl Starch Phosphate) in a concentration of 0.2% to 5% by weight based on the total weight of the preparation.

The preparations according to the invention are moreover advantageously characterized in that the preparation is in the form of an emulsion.

In such a case it is preferable according to the invention when the preparation is in the form of an oil-in-water emulsion (O/W emulsion).

In such a case the embodiments particularly preferred according to the invention are characterized in that the preparation contains one or more emulsifiers selected from the group of the compounds glyceryl stearate citrate (INCI: Glyceryl Stearate Citrate), sodium stearoyl glutamate (INCI: Sodium Stearoyl Glutamate), glyceryl stearate (INCI: Glyceryl Stearate), sodium cetearyl sulfate (INCI: Sodium Cetearyl Sulfate), glyceryl stearate SE (INCI: Glyceryl Stearate SE), sodium cetearyl sulfate (INCI: Sodium Cetearyl Sulfate), stearic acid (INCI: Palmitic Acid+Stearic Acid+Myristic Acid+Arachidic Acid+Oleic Acid), Glyceryl Stearate (INCI: Glyceryl Stearate), Polyglyceryl-3 diisostearate (INCI: Polyglyceryl-3 Diisostearate).

It is therefore advantageous according to the invention when the emulsifiers are employed in a usage concentration of 0.1% to 5% by weight based on the total weight of the preparation.

The embodiments of the present invention that are advantageous according to the invention are further characterized in that the preparation is free from polyethylene glycol ethers and esters and free from parabens, methylisothiazolinone, chloromethylisothiazolinone and DMDM hydantoin.

The preparation according to the invention should moreover preferably be free from animal constituents.

It is advantageous in the context of the present invention when the preparation contains waxes and/or fatty alcohols. According to the invention it is preferable to employ waxes/fatty alcohols from the list of the following compounds: Cetearyl Alcohol, Cetyl Alcohol, Stearyl Alcohol, *Butyrospermum parkii* Butter, Cetyl Palmitate, Methyl Palmitate, Myristyl Myristate, Hydrogenated Coco-Glycerides, Myristyl Alcohol, Behenyl Alcohol, Hydrogenated Castor Oil, *Theobroma cacao* Seed Butter, Hydrogenated Rapeseed Oil, Caprylic/Capric/Myristic/Stearic Triglyceride, Hydrogenated Vegetable Oil, Carnauba Wax, Candelilla Wax, Sunflower Wax, Tristearin.

It was moreover found that it is of particular advantage according to the invention when the preparation contains one or more lipophilic components selected from the group of the compounds Dicaprylyl Ether, Decyl Oleate, Octyldodecanol, Squalane, Triisostearin, Shea Butter Ethyl Ester, Triheptanoin, Hexyldecyl Stearate, Isoamyl Laurate.

Advantageous embodiments of the present invention are also characterized in that the preparation contains one or more alkanediols from the group of the compounds 1,2-pentanediol, 1,2-hexanediol, 1,2-octanediol, 1,2-decanediol, 2-methyl-1,3-propanediol, ethylhexylglycerin.

Embodiments of the present invention that are advantageous according to the invention are characterized in that the preparation contains one or more compounds selected from the group of the compounds alpha-lipoic acid, folic acid, phytoene, D-biotin, coenzyme Q10, alpha-glucosylrutin, carnitine, carnosine, natural isoflavonoids, flavonoids, creatine, creatinine, taurine, β-alanine, tocopherol, panthenol, magnolol, honokiol, glycerylglycose, hyaluronic acid and/or salts thereof and/or licochalcone A.

The preparations according to the invention may moreover contain further cosmetic ingredients.

It is therefore advantageous when the preparation contains fillers, in particular tapioca starch. The usage concentration for tapioca starch advantageous according to the invention is 0.05% to 3.0% by weight based on the total weight of the preparation. Tapioca starch has the advantage over other fillers, such as for example zinc oxide, that the preparation does not become too hard.

The water phase of the preparations according to the invention may advantageously contain customary cosmetic auxiliaries, for example alcohols, in particular those having a low carbon number, preferably ethanol.

DETAILED DESCRIPTION OF EXEMPLARY EMBODIMENTS OF THE INVENTION

Comparative Experiment

The following experiment demonstrated by way of example the effect according to the invention: The following formulations were produced and their whitening effect upon spreading onto the skin was investigated.

| INCI | A<br>m [%] | B<br>m [%] | C<br>m [%] |
|---|---|---|---|
| Sodium Cetearyl Sulfate | 0.15 | 0.15 | 0.15 |
| Glyceryl Stearate SE | 1.5 | 1.5 | 1.5 |
| Glyceryl Stearate | 1 | 1 | 1 |
| Cetearyl Alcohol | 4 | 4 | 4 |
| Butyrospermum Parkii Butter | 1 | 1 | 1 |
| Brassica Campestris Seed Oil | 4 | 4 | 4 |
| Dicaprylyl Ether | 4 | 4 | 4 |
| Carbomer | 0.5 | | |
| Hydroxypropyl Starch Phosphate | | 0.5 | |
| Xanthan Gum | | | 0.5 |
| Glycerin | 7 | 7 | 7 |
| Phenoxyethanol | 0.9 | 0.9 | 0.9 |
| Ethylhexylglycerin | 0.2 | 0.2 | 0.2 |
| 45% sodium hydroxide soln. | 0.06 | | |
| Aqua | ad 100 | ad 100 | ad 100 |
| Whitening effect upon spreading onto the underarm area (75 μl in each case) | strong | faint | very strong |

EXAMPLES

The following examples are intended to elucidate the present invention without limitation thereof. All reported amounts, proportions and percentages are based on the weight and the total amount/on the total weight of the preparations unless otherwise stated.

| INCI | D m [%] | E m [%] | F m [%] | G m [%] |
|---|---|---|---|---|
| Hydroxypropyl Starch Phosphate | 1.5 | 0.75 | 1 | 0.7 |
| Coco-Caprylate/Caprate | | 3 | | 2 |
| Decyl Cocoate | | | | 3 |
| Simmondsia Chinensis Seed Oil | | 3 | | |
| Vegetable Oil | 4 | | | 2 |
| Dicaprylyl Ether | 2 | 1.5 | | |
| Prunus Amygdalus Dulcis Oil | | | | 1 |
| Glycine Soja Oil | | | 3 | |
| Ricinus Communis Seed Oil | | | 2 | |
| Cocos Nucifera Oil | | | 2 | |
| Theobroma Cacao Seed Butter | | 1 | 2 | |
| Sodium Cetearyl Sulfate | 0.1 | 0.15 | | |
| Sodium Stearoyl Glutamate | | | 0.2 | 0.3 |
| Glyceryl Stearate SE | 1.7 | 2.5 | | |
| Glyceryl Stearate | | 0.5 | 3 | 2 |
| Cetearyl Alcohol | 1.2 | | 2 | |
| Stearyl Alcohol | | 3 | | 2 |
| Butyrospermum Parkii Butter | 1 | | | |
| Cetyl Palmitate | | 0.5 | | 1 |
| Glycerin | 7 | 7 | 5 | 5 |
| Phenoxyethanol | | 0.9 | | 0.9 |
| Ethylhexylglycerin | 0.2 | 0.2 | 0.4 | |
| Benzyl Alcohol | 0.2 | | | 0.2 |
| Polyglyceryl-2 Caprate | | | | 0.5 |
| Alcohol | 4 | 4 | | |
| Perfume | 0.2 | | | 0.4 |
| Aqua | balance to 100 | balance to 100 | balance to 100 | balance to 100 |

| INCI | H m [%] | I m [%] | K m [%] | L m [%] |
|---|---|---|---|---|
| Hydroxypropyl Starch Phosphate | 1 | 0.75 | 0.75 | 1 |
| Brassica Campestris Seed Oil | 5 | | | |
| Olea Europaea Fruit Oil | 2 | | | |
| Octyldodecanol | 1 | | | 0.5 |
| Vegetable Oil | | 3 | 0.6 | 0.6 |
| Prunus Amygdalus Dulcis Oil | | | 0.3 | 0.5 |
| Caprylic/Capric Triglyceride | | 3 | | |
| Decyl Oleate | | 2 | | |
| Hydrogenated Coco-Glyceride | 3 | | 0.7 | 1 |
| Cetyl Palmitate | 2 | | | |
| Glyceryl Stearate Citrate | 1 | 2 | 0.8 | |
| Glyceryl Stearate | | 1 | | 1 |
| Palmitic Acid + Stearic Acid + Myristic Acid + Arachidic Acid + Oleic Acid | | | 2 | 0.8 |
| Myristyl Alcohol | | | 5 | |
| Cetearyl Alcohol | 2 | 3 | | |
| Stearyl Alcohol | | | | |
| Cetyl Alcohol | | | | 3.5 |
| Tristearin | | | 0.8 | 1.2 |
| Glycerin | 7 | 10 | 5 | 4 |
| Phenoxyethanol | | 0.8 | 0.9 | |
| Ethylhexylglycerin | 0.5 | | | 0.3 |
| Benzyl Alcohol | | 0.1 | | |
| Levulinic Acid | 0.2 | | | |
| Alcohol Denat. | 4 | | 3 | 4 |
| Perfume | 0.3 | 0.4 | 0.15 | 0.2 |
| Aqua | balance to 100 | balance to 100 | balance to 100 | balance to 100 |

What is claimed is:

1. A cosmetic preparation, wherein the preparation comprises (a) hydroxypropyl starch phosphate and (b) one or more vegetable oils which comprise one or more of *Persea gratissima* Oil, *Orbignya oleifera* seed oil, *Argania spinosa* Kernel Oil, *Prunus armeniaca* Kernel Oil, *Simmondsia chinensis* seed oil, *Cocos nucifera* Oil, *Silybum marianum* seed oil, *Oenothera biennis* Oil, *Olea europaea* Fruit Oil, *Helianthus annuus* seed oil, *Vitis vinifera* seed oil, *Cannabis sativa* seed oil, *Gossypium herbaceum* seed oil, *Arctium lappa* seed oil, *Macadamia ternifolia* seed oil, *Macadamia integrifolia* seed oil, *Zea mays* Germ Oil, *Prunus amygdalus dulcis* Oil, *Ricinus communis* seed oil, *Glycine soja* Oil, *Helianthus annuus* Hybrid Oil, *Sesamum indicum* seed oil, *Brassica campestris* seed oil, a weight ratio (a):(b) being from 2:1 to 1:20 and the preparation being free from mineral oils, silicone oils, polyacrylates and xanthan gum.

2. The preparation of claim 1, wherein a weight ratio (a):(b) is from 1:1 to 1:10.

3. The preparation of claim 1, wherein the preparation further comprises one or more esters of caprylic acid and/or capric acid.

4. The preparation of claim 1, wherein the composition further comprises one or more compounds selected from caprylic acid/capric acid triglycerides, caprylyl caprylate/ caprate, coco caprylate/caprate, coco glycerides, ethylhexyl cocoate, decyl cocoate, isoamyl cocoate, dicaprylyl carbonate, coco caprylate.

5. The preparation of claim 1, wherein the preparation comprises from 0.2% to 5% by weight of (a), based on a total weight of the preparation.

6. The preparation of claim 1, wherein the preparation is in the form of an emulsion.

7. The preparation of claim 1, wherein the preparation is in the form of an oil-in-water (O/W) emulsion.

8. The preparation of claim 1, wherein the preparation is free from polyethylene glycol ethers and esters and free from parabens, methylisothiazolinone, chloromethylisothiazolinone and DMDM hydantoin.

9. The preparation of claim 1, wherein the preparation further comprises waxes and/or fatty alcohols.

10. The preparation of claim 1, wherein the preparation further comprises one or more emulsifiers selected from glyceryl stearate citrate, sodium stearoyl glutamate, glyceryl stearate, sodium cetearyl sulfate, glyceryl stearate SE, sodium cetearyl sulfate, stearic acid, Glyceryl Stearate, Polyglyceryl-3 diisostearate.

11. The preparation of claim 10, wherein the preparation comprises the one or more emulsifiers in a concentration of from 0.1% to 5% by weight based on a total weight of the preparation.

12. The preparation of claim 1, wherein the preparation is free from animal-derived constituents.

13. The preparation of claim 1, wherein the preparation further comprises one or more lipophilic components selected from dicaprylyl ether, decyl oleate, octyldodecanol, squalane, triisostearin, shea butter ethyl ester, triheptanoin, hexyldecyl stearate, isoamyl laurate.

14. The preparation of claim 1, wherein the preparation further comprises one or more of 1,2-pentanediol, 1,2-hexanediol, 1,2-octanediol, 1,2-decanediol, 2-methyl-1,3-propanediol, ethylhexylglycerin.

15. The preparation of claim 1, wherein the preparation further comprises one or more fillers.

16. The preparation of claim 15, wherein the one or more fillers comprise tapioca starch.

17. The preparation of claim 1, wherein the preparation further comprises ethanol.

18. A method of substituting mineral and silicone oils in a cosmetic preparation, wherein the method comprises using hydroxypropyl starch phosphate and one or more vegetable oils selected from *Persea gratissima* Oil, *Orbignya oleifera* seed oil, *Argania spinosa* Kernel Oil, *Prunus armeniaca* Kernel Oil, *Simmondsia chinensis* seed oil, *Cocos nucifera* Oil, *Silybum marianum* seed oil, *Oenothera biennis* Oil, *Olea europaea* Fruit Oil, *Vitis vinifera* seed oil, *Cannabis sativa* seed oil, Olus Oil, *Gossypium herbaceum* seed oil, *Arctium lappa* seed oil, *Macadamia ternifolia* seed oil, *Macadamia integrifolia* seed oil, *Zea mays* Germ Oil, *Prunus amygdalus dulcis* Oil, *Ricinus communis* seed oil, *Glycine soja* Oil, *Sesamum indicum* seed oil, *Brassica campestris* seed oil instead of the mineral and silicone oils.

19. A cosmetic preparation, wherein the preparation is in the form of an emulsion and comprises (a) hydroxypropyl starch phosphate and (b) one or more vegetable oils a weight ratio (a):(b) being from 2:1 to 1:20 and the preparation being free from mineral oils, silicone oils, polyacrylates and xanthan gum.

20. The preparation of claim 19, wherein the preparation further comprises one or more lipophilic components selected from dicaprylyl ether, decyl oleate, octyldodecanol, squalane, triisostearin, shea butter ethyl ester, triheptanoin, hexyldecyl stearate, isoamyl laurate.

* * * * *